United States Patent [19]
Yoon

[11] Patent Number: 5,324,268
[45] Date of Patent: Jun. 28, 1994

[54] TROCAR WITH SAFETY SHIELD

[76] Inventor: InBae Yoon, 2101 Highland Ridge Dr., Phoenix, Md. 21131

[21] Appl. No.: 808,325

[22] Filed: Dec. 16, 1991

[51] Int. Cl.⁵ .......................................... A61M 5/178
[52] U.S. Cl. .......................................... 604/158
[58] Field of Search ................. 604/164, 167, 93, 110, 604/198, 158

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. ........................ 604/164 |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander ........................... 606/185 X |
| 5,053,016 | 10/1991 | Lander . |
| 5,061,251 | 10/1991 | Juhasz . |
| 5,066,288 | 11/1991 | Deniega et al. ........................ 604/274 |
| 5,104,382 | 4/1992 | Brinkerhoff et al. . |
| 5,104,383 | 4/1992 | Shichman ........................ 604/167 |
| 5,114,407 | 5/1992 | Burbank ........................ 604/164 |
| 5,116,353 | 5/1992 | Green . |
| 5,127,909 | 7/1992 | Shichman . |
| 5,152,754 | 10/1952 | Plyley et al. . |
| 5,158,552 | 10/1992 | Borgia et al. . |

FOREIGN PATENT DOCUMENTS 2544262 4/1977 Fed. Rep. of Germany .
1435246 11/1988 U.S.S.R. .

*Primary Examiner*—Gene Mancene
*Assistant Examiner*—Jeffrey A. Smith

[57] ABSTRACT

A retractable safety penetrating instrument with safety shield for introducing a portal sleeve into a cavity in the body includes a portal sleeve, a trocar disposed within the portal sleeve and a safety shield disposed between the portal sleeve and the trocar and having a distal end biased to protrude beyond a sharp distal end of the trocar. The trocar is supported in a manner to automatically move proximally from an extended position wherein the sharp distal end protrudes from the portal sleeve to a retracted position wherein the sharp distal end is protected within the retractable safety penetrating instrument in response to distal movement of the safety shield upon penetration into a cavity in the body. A retracting mechanism moves the trocar proximally and is normally locked in a position preventing proximal movement of the trocar and is released by distal movement of an operating member to trigger retraction of the trocar.

40 Claims, 2 Drawing Sheets

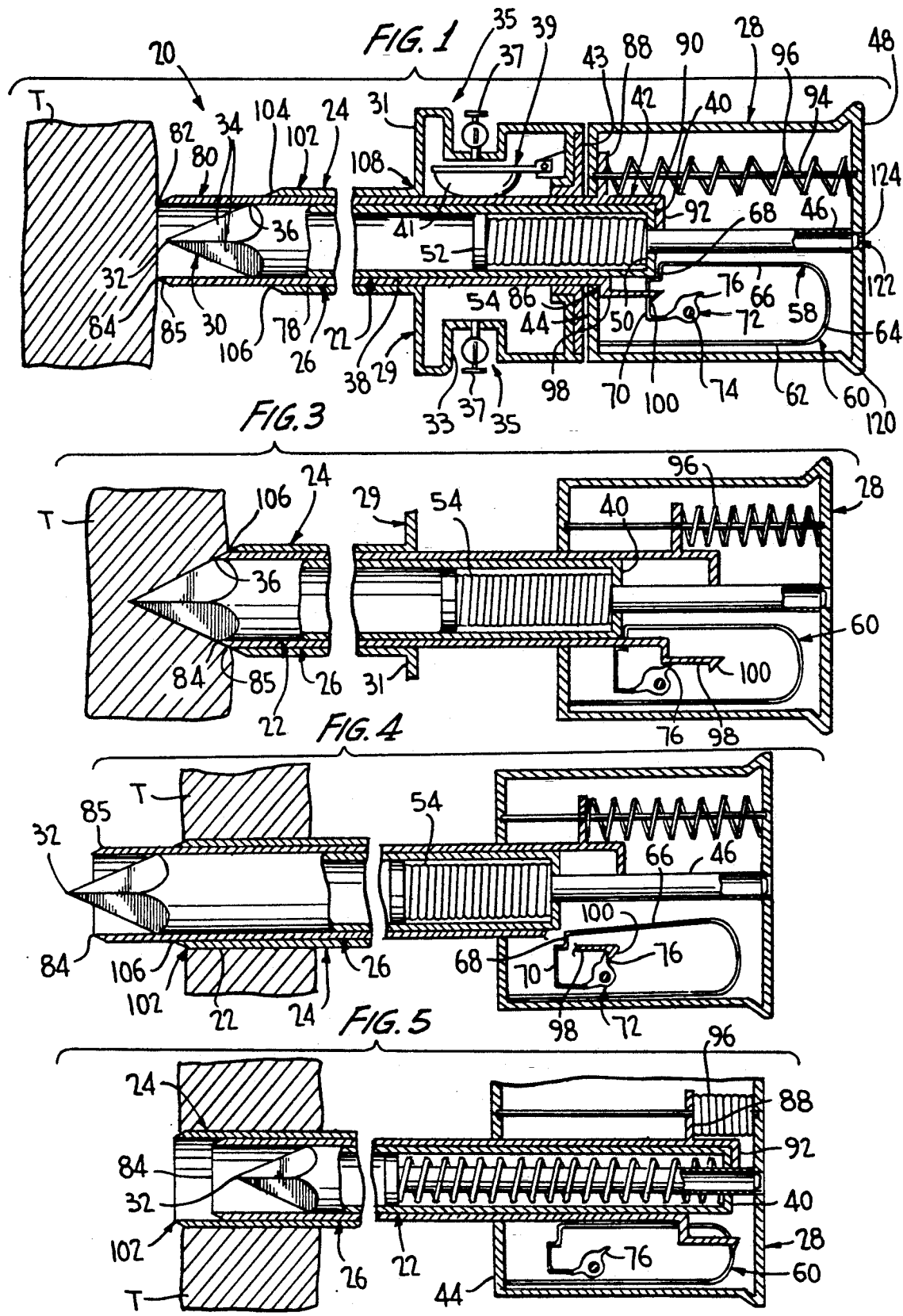

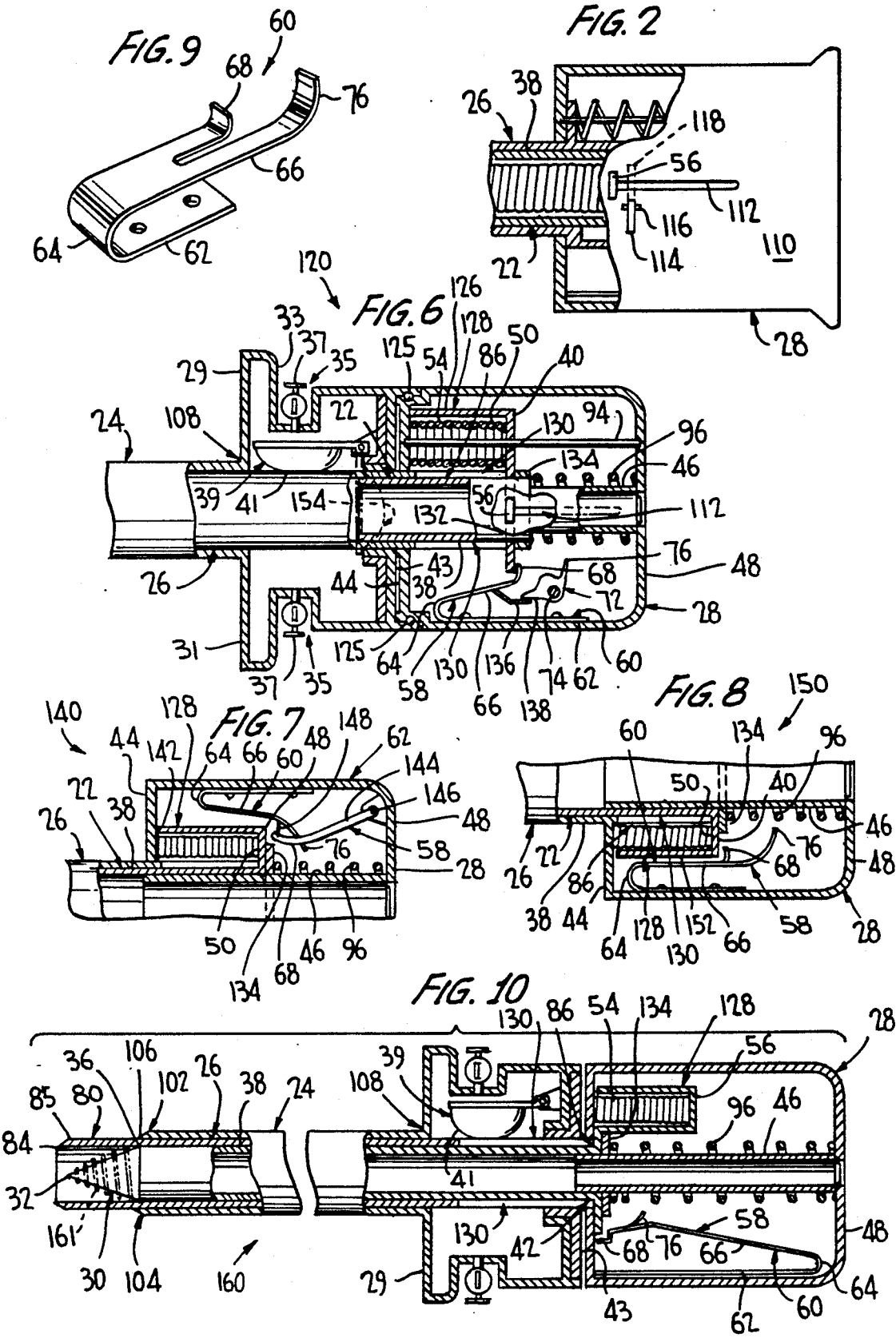

TROCAR WITH SAFETY SHIELD

BACKGROUND OF THE INVENTION

1. Field of the Invention

The present invention pertains to safety penetrating instruments and, more particularly, to safety penetrating instruments having portal sleeves, penetrating members disposed within the portal sleeves and having sharp tips for penetrating cavity walls and safety shields disposed between the portal sleeves and the penetrating members, with the sharp tips of the penetrating members being automatically protected upon penetration to protect tissue and organ structures within the cavities.

2. Discussion of the Prior Art

Penetrating instruments are widely used in medical procedures to gain access to anatomical cavities of various sizes; and, in particular, use of penetrating instruments has become an extremely popular and important first step in endoscopic, or least invasive, procedures to establish an endoscopic portal for many various procedures, most notably laparoscopy procedures, with access being established via a portal sleeve positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, No. 4,601,710 to Moll and No. 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

While prior art safety penetrating instruments are widely used, they suffer from many disadvantages when used in the procedures for which they are presently recommended; and, additionally, prior art safety penetrating instruments cannot be used in many procedures for which safety of penetration is highly desirable along with introduction of a portal sleeve. One of the disadvantages of prior art safety penetrating instruments is that the safety shields protrude from the sharp tips of the trocars to protect the sharp tips upon penetration through tissue of a cavity wall such that use in penetrating small or narrow anatomical cavities is not feasible. Another disadvantage of prior art safety penetrating instruments is that the safety shields can produce an irregular surface or profile with the portal sleeves and the sharp tips of the trocars during penetration of tissue, resulting in increased resistance from tissue during penetration of the cavity wall, trauma and damage to tissue and possible jamming and trapping of tissue.

SUMMARY OF THE INVENTION

Accordingly, it is a primary object of the present invention to overcome the above-mentioned disadvantages of prior art safety penetrating instruments.

Another object of the present invention is to automatically retract a trocar of a retractable safety penetrating instrument to a protected position in response to distal movement of a safety shield upon penetration into a body cavity.

A further object of the present invention is to arrange a safety shield in a retractable safety penetrating instrument such that movement of the safety shield distally causes a trocar to retract to a protected, safe position within the instrument.

It is also an object of the present invention to automatically retract a trocar of a retractable penetrating instrument to a protected position in response to distal movement of a safety shield prior to the safety shield protruding beyond the sharp tip of the trocar upon penetration into an anatomical cavity.

The present invention has an additional object of allowing safe introduction of a portal sleeve into body cavities of very small size, such as synovial, pleural or pericardial cavities, for example, by automatically retracting the sharp tip of a retractable safety penetrating instrument after the cavity is penetrated thereby minimizing the extension of the safety penetrating instrument into the cavity.

Yet another object of the present invention is to provide a method of safely penetrating various anatomical cavities by automatically retracting a trocar upon entry into a cavity in response to a mechanical distal movement of a safety shield of a retractable safety penetrating instrument.

It is also an object of the present invention to provide a retractable trocar with safety shield having a distally biased safety shield and a trocar disposed within the safety shield and having a sharp tip retractable with the safety shield to a safe, protected position in response to movement of the safety shield due to the distal bias upon penetration through tissue of a cavity wall.

Some of the advantages of the present invention over the prior art are that small or narrow anatomical cavities can be safely penetrated, an endoscopic portal can safely be introduced into anatomical cavities of various sizes to expand the use of least invasive procedures in many areas including, for example, cardiac, brain, vascular, chest, genitourinary system and spinal fields, safe penetration of cavities can be accomplished with no parts of the retractable trocar with safety shield protruding beyond the sharp tip of the trocar as is particularly desirable where organ structures adhere to cavity walls, the retractable trocar with safety shield encourages the use of a smooth, continuous penetrating motion by the surgeon thereby reducing trauma, tears and irregular surfaces in the tissue of the cavity wall, the retractable trocar with safety shield can be used to penetrate anatomical cavities of the type containing organ structures that could be injured by contact with even a blunt instrument part, the sharp tip of the trocar is in a protected, safe position prior to penetration of tissue ensuring safety of medical personnel during use, with the use of a threaded distal tip on the trocar, penetration of the narrowest of anatomical cavities can be achieved in a safe manner in view of the gradual advancement of the trocar coupled with immediate, automatic retraction of the trocar upon penetration into the cavity, safe penetration is achieved while permitting injection or evacuation of fluids, a single puncture can be used for both insufflation and forming an endoscopic portal thereby simplifying diagnostic and surgical procedures, trauma and damage to tissue is minimized, tissue jamming and trapping is avoided and retractable trocars with safety shields according to the present invention can be inexpensively manufactured to be reusable or disposable for universal use.

The present invention is generally characterized in a retractable trocar with safety shield including a portal sleeve, a trocar disposed within the portal sleeve and having a sharp distal tip for penetrating tissue and a safety shield disposed between the portal sleeve and the trocar and biased to an extended position protruding distally from the sharp tip of the trocar. The safety shield is movable proximally against the distal bias during penetration of tissue of a cavity wall and movable distally thereafter, with the safety shield and the sharp tip of the trocar automatically moving proximally to a safe, retracted position in response to the distal movement prior to the safety shield protruding beyond the sharp tip of the trocar. Retraction of the trocar is caused by a strong bias spring that is normally locked in a compressed state by a latch and is released by the distal movement of the safety shield to trigger the retraction of the trocar. The latch and trigger are spring loaded to normally lock the trocar against retraction and to be moved out of locking engagement by flexing of the spring via movement of a cam, an off-center rotating member or pivot or a leaf of a spring in response to the distal movement.

These and other objects and advantages of the present invention will become apparent from the following description of the preferred embodiments taken in conjunction with the accompanying drawings.

BRIEF DESCRIPTION OF THE DRAWINGS

FIG. 1 is a broken side view, partly in section, of a retractable trocar with safety shield according to the present invention.

FIG. 2 is a broken view, partly in section, of a hub of the retractable trocar with safety shield of FIG. 1.

FIGS. 3, 4 and 5 are broken side views, partly in section, showing the relative position of the trocar, the portal sleeve and the safety shield of the retractable trocar with safety shield of FIG. 1 during sequential stages of penetration of tissue of the cavity wall, and showing stages of operation for the operating member, the retracting mechanism and the locking and releasing mechanism corresponding to the stages of penetration.

FIG. 6 is a broken sectional view of a proximal end of a modification of a retractable trocar with safety shield according to the present invention.

FIG. 7 is a broken sectional view of the hub of a further modification of a retractable trocar with safety shield according to the present invention.

FIG. 8 is a broken sectional view of the hub of another modification of a retractable trocar with safety shield according to the present invention.

FIG. 9 is a perspective view of a locking and releasing mechanism of the retractable trocar with safety shield of FIG. 8.

FIG. 10 is a broken side view, partly in section, of a further modification of a retractable trocar with safety shield according to the present invention.

DESCRIPTION OF THE PREFERRED EMBODIMENTS

A retractable trocar with safety shield according to the present invention is illustrated at 20 in FIG. 1 and includes an elongate penetrating member such as trocar 22, a portal sleeve 24 concentrically disposed around trocar 22, a safety shield 26 concentrically disposed between trocar 22 and portal sleeve 24, a hub 28 mounting trocar 22 and safety shield 26 and a housing 29 mounting portal sleeve 24. The hub 28 can be latched to housing 29 with the use of any suitable releasable mechanism, such as ball detents 125 shown in FIG. 6, allowing the hub to be removed from the housing withdrawing the trocar and the safety shield from the portal sleeve. Accordingly, the retractable trocar with safety shield 20 can be considered to be formed of a portal unit and a trocar unit, the portal unit including portal sleeve 24 and housing 29 and the trocar unit including trocar 22, safety shield 26 and hub 28.

Penetrating member 22 is preferably made of stainless steel with a cylindrical body having an outer diameter dependent upon the surgical procedure to be performed and the anatomical cavity to be penetrated. The penetrating member 22 has a distal end 30 terminating at a sharp tip 32 for penetrating anatomical tissue. The distal end 30 can have various configurations; and, as shown in FIG. 1, the distal end 30 is formed as a trocar with a pyramidal shape defined by three, equally spaced end surfaces or facets 34 tapering distally to sharp tip 32 and terminating proximally at scalloped edges or junction 36 joining the facets to an elongated, cylindrical body 38. Cylindrical body 38 extends proximally from junction 36 to a proximal end 42 of the trocar 22, the proximal end 42 being disposed in hub 28 with cylindrical body 38 passing through an aperture in a front wall 44 of the hub. The proximal end 42 of the trocar 22 is hollow to be mounted on a cylindrical member or tube 46 extending distally from an end wall 48 of hub 28 into the hollow proximal end 42 of the trocar. A retracting mechanism is disposed at the proximal end 42 and includes an end face or plate 40 defining an internal, annular abutment wall 50 extending radially inwardly from a wall of the cylindrical body 38, the tube 46 extending through an opening in plate 40 into proximal end 42. An annular rim 52 is formed on tube 46 to be disposed in the proximal end 42 of the trocar 22, and a helical, coil retracting spring 54 is disposed around tube 46 and mounted in compression between rim 52 and abutment wall 50 to bias the trocar 22 in a proximal direction. To simplify assembly of the retractable trocar with safety shield, plate 40 can be removably attached to cylindrical body 38 such as by threads and the like. As shown in FIG. 2, a knob 56 is threadedly secured along the periphery of the cylindrical body 38 of the trocar 22 at plate 40. Cylindrical body 38 can be hollow or tubular along the length of the trocar or the cylindrical body can be partly hollow or tubular depending upon manufacturing techniques utilized and the construction of the distal end 30 of the trocar. While the distal end of the trocar is shown having a solid, pyramidal configuration, the distal end configuration can have other solid or hollow geometric configurations, such as the conical or threaded configurations shown in FIG. 10, and the distal end can be provided with apertures establishing fluid communication with an anatomical cavity. The distal end of the trocar can be removably mounted on cylindrical body 38 allowing various distal tips to be interchangeably mounted on the cylindrical body.

A locking and releasing mechanism 58 for the retracting mechanism is disposed in hub 28 and includes a latch or locking spring 60 having a substantially flat base 62 secured to a side wall of hub 28 and terminating proximally at an arcuate bend 64 proximate end wall 48 of the hub and an arm 66 joined to bend 64 and extending distally therefrom toward plate 40 parallel with a longitudinal axis of the retractable trocar with safety shield. A bent locking finger 68 on a distal end of the arm 66 engages plate 40 and prevents movement of the retracting mechanism and, therefore, trocar 22, in a proximal direction thereby locking the retracting spring 54 in a compressed state. Latch 60 has a connecting web 70 joining the finger 68 to a releasing or trigger member such as an off-center pivot or cam 72 mounted in hub 28. Cam 72 is rotatably mounted on a pin 74 extending transverse to arm 66 and having ends secured to side walls of the hub, the pin 74 passing through the cam 72 off-center with a central longitudinal axis of the cam. A trigger or leaf 76 extends angularly, proximally from cam 72, the cam being positioned by arm 66 such that the trigger 76 is disposed in a rest position with finger 68 engaging plate 40 as shown in FIG. 1. Arm 66 can bias cam 72 and, therefore, trigger 76, to the rest position or a spring (not shown) can be disposed around pin 74 and secured to cam 72 and a side wall of hub 28, respectively, with a torsional bias to bias the cam to the rest position. The latch can be mounted at any suitable location on the hub and provided with a configuration to act as a stop or abutment to prevent proximal movement of the retracting mechanism and, therefore, the trocar, and to be actuated or released by a trigger. The latch and trigger can be made as one piece or multiple pieces dependent upon the hub construction and the operating member for engaging the trigger as will be discussed further below. Although the web 70 is shown joined to cam 72, web 70 can be formed as a contacting member frictionally contacting or engaging portion of cam 72.

Safety shield 26 is preferably made of a cylindrical length of suitable, medically acceptable, plastic or metal material and can be rigid or flexible and transparent or opaque. The safety shield includes a cylindrical body 78 concentrically disposed around trocar 22 and having a distal end 80 that can be acutely angled or beveled from a trailing edge 85 to a distal peripheral edge 84 as shown at 82 in FIG. 1 and a proximal end 86 disposed in hub 28. Cylindrical body 78 has an outer diameter sized to be closely received in the portal sleeve and an inner diameter sized to closely receive the outer diameter of the trocar such that there is minimal gap between the safety shield, the portal sleeve and the trocar. Cylindrical body 78 terminates at a flange 88 mounted on proximal end 86 to extend outwardly from the cylindrical body 78, and an extension or ledge 90 axially aligned with a wall of the cylindrical body 78 extends perpendicularly from flange 88 along the trocar 22 in a proximal direction. Ledge 90 terminates proximally at a shoulder 92 extending inwardly, perpendicularly from the ledge 90 in the direction of the longitudinal axis of the retractable trocar with safety shield, the shoulder 92 being disposed proximally of plate 40. A connecting bar 94 has ends secured to front wall 44 and end wall 48 of hub 28, respectively, with the connecting bar 94 passing through an aperture in flange 88. A helical spring 96 is disposed around the connecting bar 94 and mounted in compression between flange 88 and end wall 48 to bias the safety shield in a distal direction with shoulder 92 biased against plate 40 and flange 88 biased against front wall 44 of hub 28 as shown in FIG. 1. An operating member is disposed on safety shield 26 diametrically opposite ledge 90 and includes an operating or cocking arm 98 extending perpendicularly in a proximal direction from flange 88 parallel with the longitudinal axis, the operating arm 98 terminating at a hook 100. The operating arm 98 is positioned in hub 28 such that the trigger 76 in the rest position is disposed in the path of axial movement of the operating arm 98.

Hub 28 is preferably made of plastic to reduce cost and has an external configuration to be easily grasped with one hand for use in penetrating tissue. Hub 28 can be substantially rectangular in cross-section including four side walls extending from front wall 44 to end wall 48 with one side wall, indicated at 110 in FIG. 2, having a slot 112 therein disposed parallel with a longitudinal axis of the retractable trocar with safety shield and receiving knob 56. A lock 114 is mounted externally along wall 110 on a hinge 116 such that the lock 114 can be pivoted between an unlocked position wherein the lock does not block movement of knob 56 along slot 112 and a locked position shown in broken lines at 118 wherein the lock is disposed transverse to slot 112 to abut a proximal face of knob 56 to block proximal movement of the knob and, therefore, the trocar 22. The side walls of the hub 28 can be flared as shown in FIG. 1 at 120 providing a flared external profile adjacent end wall 48. A valve assembly 122, such as rotatable valve 124, is provided in end wall 48 of the hub in alignment with the lumen of tube 46 to allow passage of fluid therethrough for additional confirmation of cavity penetration via leakage detection and for irrigation and aspiration when the trocar is hollow therealong and is provided with one or more apertures at distal end 30 establishing fluid communication between the lumen of tube 46 and an anatomical cavity.

Portal sleeve 24 is preferably made of a cylindrical length of stainless steel or other suitable, medically acceptable, plastic or metal material and can be rigid or flexible and transparent or opaque. The portal sleeve has a distal end 102, that can be acutely angled or beveled at the same angle as distal end 80 of safety shield 26 terminating distally at a peripheral edge 106, as shown at 104 in FIG. 1, and a proximal end 108 secured to a front wall 31 of housing 29. The portal sleeve 24 has an outer diameter typically ranging in size from 5 mm to 12 mm and an inner diameter sized to closely receive the outer diameter of the safety shield such that there is minimal gap or space between the portal sleeve and the safety shield.

Housing 29 is preferably made of plastic to reduce cost and has a configuration in cross-section corresponding to the cross-sectional configuration of hub 28 with a flared intermediate wall 33 proximally spaced from front wall 31 producing a flared external profile adjacent front wall 31 facilitating grasping during use. Recesses 35 are formed in the housing 29 proximally of intermediate wall 33 and have a size and configuration to receive ball-type stop cocks 37, respectively, in a position such that the stop cocks are protected from inadvertent contact which could cause breakage or malfunction. A valve assembly 39 is mounted in housing 29 to control flow through the portal sleeve and the housing once the trocar unit is removed therefrom. The valve assembly 39 can have any acceptable configuration and, as shown, includes a flapper valve 41 biased to close off and seal an opening in an end wall 43 of the housing as shown in broken lines at 154 in FIG. 6.

In order to assemble the retractable penetrating instrument 20, the safety shield 26 is mounted on the trocar 22, and the proximal end 86 of the safety shield 26 is assembled in hub 28 as shown in FIG. 1 with the safety shield biased distally by spring 96 such that flange 88 is biased against front wall 44 of hub 28 and shoulder 92 is biased against plate 40 of the trocar 22. The retracting mechanism and, therefore, the trocar 22, is prevented from moving proximally by the locking and releasing mechanism 58 via engagement of finger 68 with plate 40. Hook 100 of operating arm 98 is disposed distally of trigger 76 with the trigger 76 and cam 72 in the rest position. The trocar unit formed by the trocar, the safety shield and the hub is then combined with the portal unit passing the safety shield through the housing 29 via the opening in end wall 31 while simultaneously opening valve 41, and through the portal sleeve 24. With the front wall 44 of hub 28 abutting the end wall 31 of housing 29, the sharp tip of the trocar will protrude beyond the peripheral edge 106 of the portal sleeve and the peripheral edge 84 of the safety shield will protrude beyond and protect the sharp tip 32 of the trocar.

In a method of operation for the retractable trocar with safety shield 20, the latch 60 is normally in the position shown in FIG. 1 with trigger 76 in the rest position and finger 68 engaging plate 40 of the trocar such that the retracting spring 54 is compressed and the trocar cannot move proximally and is, therefore, locked. Spring 96 is normally in the position shown in FIG. 1 such that the safety shield 26 is biased distally with peripheral edge 84 disposed distally of sharp tip 32 of the trocar as shown in FIG. 1 just prior to penetration of tissue T of an anatomical cavity wall. When tissue T is to be penetrated, the hub 28 and housing 29 are gripped in one hand and the retractable penetrating instrument is forced into the tissue T as shown in FIG. 3. The safety shield 26 will move proximally against the distal bias of spring 96 due to the proximal force from tissue contact at the distal end of the retractable safety penetrating instrument such that the peripheral edge 84 of the safety shield will be substantially aligned with junction 36 of the trocar 22 and the trailing edge 85 of the safety shield will be substantially aligned with the peripheral edge 106 of the portal sleeve 24 presenting a substantially smooth profile facilitating penetration of tissue and minimizing tissue jamming and trapping. Operating arm 98 will have moved axially, proximally within hub 28 such that hook 100 is positioned proximally of trigger 76. During movement past the trigger 76, operating arm 98 urges the trigger clockwise looking at FIG. 3; however, this movement does not disengage the latch 60 from the plate 40 and the trigger returns to the rest position as soon as the operating arm 98 has moved proximally therepast. Accordingly, the trocar, the safety shield and the portal sleeve will be stable and move together through the tissue. Once the distal end 102 of the portal sleeve 24 has entered the anatomical cavity, as shown in FIG. 4, such that the force from tissue contact is removed from the distal end of the retractable safety penetrating instrument, the safety shield 26 will be moved distally due to the distal bias of spring 96. As the safety shield 26 moves distally, operating arm 98 moves axially, distally such that hook 100 engages trigger 76 and pulls the trigger distally causing the cam 72 to rotate counterclockwise looking at FIG. 4. With counterclockwise rotation, cam 72 pulls arm 66, via the connecting web 70, in a direction angularly, outwardly from the longitudinal axis and toward base 62 such that finger 68 is released from engagement with plate 40 prior to peripheral edge 84 of the safety shield protruding beyond the sharp tip 32 of the trocar. Once the finger 68 is released, the trocar 22 will move proximally along the tube 46 due to the proximal bias of retracting spring 54, the tube 46 guiding proximal movement of the trocar. The trocar 22 will carry the safety shield 26 proximally due to the abutment of plate 40 with shoulder 92, the strong retracting spring 54 overriding the distal bias of spring 96. With the trocar 22 moved proximally by the retracting mechanism, the sharp tip 32 of the trocar and the peripheral edge 84 of the safety shield are retracted within the distal end 102 of the portal sleeve 24, and the hook 100 of operating arm 98 is positioned proximally of trigger 76, the trigger having returned to the rest position. The trocar unit can be removed from the portal sleeve unit leaving the portal sleeve in place allowing insertion of additional instruments, irrigation, aspiration and other procedures to be conducted via the opening in the end wall 43 of valve housing 29. When it is desired to reset the retractable safety penetrating instrument for further use, the knob 56 is grasped and manually moved distally along the slot 112 in hub 28 moving the trocar distally past the trigger 76 until flange 88 abuts front wall 44 of the hub 28 and the finger 68 of the latch 60 engages the plate 40 to lock the retracting mechanism and prevent proximal movement of the trocar. The safety shield will then be biased distally by spring 96 such that the sharp tip 32 of the trocar is protected.

By varying the axial position of trigger 76 in the path of movement of the operating arm 98, the distance that the safety shield can move distally before the operating member releases the retracting mechanism upon penetration into an anatomical cavity can be controlled. In other words, trigger 76 can be positioned in hub 28 such that the peripheral edge 84 of the safety shield 26 does not protrude beyond the sharp tip 32 of the trocar 22 before the retracting mechanism is released. Accordingly, the distance that the peripheral edge 84 of the safety shield is allowed to move distally upon penetration into an anatomical cavity can be varied or adjusted by positioning the trigger 76 to be disposed a greater or lesser distance from hook 100 after the operating arm 98 has moved proximally during penetration. With the trigger 76 positioned distally of hook 100 a lesser distance, the safety shield 26 will move distally a minimal distance before the retracting mechanism is released and, with the trigger 76 positioned distally of hook 100 a greater distance, the safety shield will move distally a relatively greater distance before the operating member triggers the retracting mechanism. The safety shield need move distally only a minimal distance before triggering the retracting mechanism such that the safety shield does not protrude beyond the sharp tip of the trocar upon penetration into the anatomical cavity thereby minimizing the distance that the retractable penetrating instrument protrudes into the cavity.

Although springs 54 and 96 are shown as coil springs, other types and configurations of springs as well as various other devices can be utilized to bias the trocar and the safety shield. It will be appreciated that the trocar and the safety shield can be biased in many ways and that springs 54 and 96 can be replaced with various devices including flexible, compressible and resilient devices and materials, such as sponge and rubber, capable of applying a biasing force.

It will be appreciated that knob 56 is shown by way of example, and that many other types of knobs or handles can be employed for resetting the retractable safety penetrating instrument. As a further example, an L-shaped handle can be attached to trocar 22 allowing the slot 112 to be located at various other positions along the side walls of the hub 28 and not only the central position shown in FIG. 2.

Where it is desired to lock the trocar 22 such that the trocar does not retract upon penetration into the anatomical cavity, lock 114 can be pivoted 180° from the unlocked position to the locked position shown in broken lines in FIG. 2 preventing proximal movement of the trocar when finger 68 is disengaged from plate 40. It will be appreciated that lock 56 is shown by way of example and that other locking devices can be utilized to optionally prevent retraction of the trocar.

Numerous other types of releasing or trigger members can be utilized in addition to cam 72 for releasing or disengaging the latch 58 from the retracting mechanism. The locking and releasing mechanism 56 can be of multi-part construction or of integral, unitary construction. Various types of actions including camming, bending, buckling and spring actions can be employed for releasing the latch 60 from the retracting mechanism.

It will be appreciated that the retracting mechanism, the locking and releasing mechanism, the operating member and the distal end configuration of the penetrating members are illustrative only and that the retracting mechanism, the locking and releasing mechanism, the operating member and the penetrating member distal end can have various structural configurations and arrangements including those disclosed in applicant's co-pending patent application entitled "Retractable Safety Penetrating Instrument for Portal Sleeve Introduction" filed on Nov. 27, 1991 and incorporated herein by reference.

A modification of a retractable trocar with safety shield according to the present invention is illustrated in FIG. 6 at 120, the proximal end of the retractable trocar with safety shield 120 being shown. The retractable trocar with safety shield 120 includes trocar 22, portal sleeve 24 concentrically disposed around trocar 22, safety shield 26 concentrically disposed between portal sleeve 24 and safety shield 26, hub 28 mounting trocar 22 and safety shield 26 and housing 29 mounting portal sleeve 24.

The trocar 22 includes a cylindrical body 38 passing through an opening in front wall 44 of hub 28 and a hollow proximal end 42 disposed in the hub, with tube 46 extending distally from end wall 48 of the hub into the proximal end of the trocar. A retracting mechanism is mounted on the trocar 22 within hub 28 and includes a plate or flange 40 at proximal end 42 extending outwardly from the cylindrical body 38 of the trocar, an abutment wall 50 on plate 40 disposed parallel with front wall 44 of hub 28 and a flat side 126 extending perpendicularly, distally from plate 40 toward front wall 44 to define a rail 128 for mounting strong retracting spring 54. A connecting bar 94 has ends secured to front wall 44 and end wall 48, respectively, of hub 28, the connecting bar extending longitudinally through the rail via an opening in abutment wall 50. Retracting spring 54 is disposed around the connecting bar 94 and mounted in compression between front wall 44 and abutment wall 50 to bias the retracting mechanism and, therefore, the trocar, in the proximal direction. The safety shield 26 terminates proximally at an operating member 134 at a proximal end 86 of the safety shield, the safety shield extending proximally through an opening in plate 40 with plate 40 extending through a pair of diametrically opposed, longitudinal slots 130 in the cylindrical body 78 of the safety shield. The operating member includes an edge 132 on the cylindrical body 78 of the safety shield formed by a wall of the cylindrical body at a proximal end of one of the slots 130. A spring 96 is disposed around tube 46 and mounted in compression between the operating member 134 and the end wall 48 of hub 28 to bias the safety shield in the distal direction such that edge 132 is biased against plate 40. A locking and releasing mechanism 58 mounted in hub 28 prevents proximal movement of the retracting mechanism and includes a latch or locking spring 60 having a substantially flat base 62 secured to a wall of hub 28 and terminating at a distal bend 64 and an arm 66 extending angularly, proximally from bend 64 in the direction of the longitudinal axis of the retractable trocar with safety shield. Arm 66 is bifurcated at a proximal end thereof to form a curved locking finger 68 biased into engagement with plate 40 to prevent proximal movement of the retracting mechanism and a contacting finger 136 extending proximally from the arm and positioned in engagement with a releasing or trigger member including a cam 72 or off-center pivot. Cam 72 is mounted in hub 28 on a pin 74 extending transverse to the longitudinal axis of the retractable safety penetrating instrument and having ends secured to side walls of the hub 28, the pin 74 passing through the cam 72 off-center with a longitudinal axis of the cam. An actuating member 138 extends distally from a distal portion of the cam 72, the actuating member engaging the contacting finger 136 with the cam 72 in a rest position. A trigger or leaf 76 extends outwardly from a proximal portion of the cam toward the longitudinal axis of the retractable trocar with safety shield, the trigger being disposed in a rest position with the cam such that the trigger is in the path of movement of the operating member 134. Latch 60 can bias the cam 72, via engagement of contacting finger 136 with actuating member 138, to the rest position, or the cam can be torsionally biased to the rest position with a spring (not shown) mounted on pin 74 and secured to cam 72 and a side wall of hub 28, respectively. Portal sleeve 24 has a distal end 102 terminating at peripheral edge 106 and a proximal end 108 secured to a front wall 31 of housing 29.

In order to assemble the retractable trocar with safety shield 120, the proximal end 42 of the trocar 22 is assembled in hub 28 as shown in FIG. 6 with plate 40 of the retracting mechanism held by latch 60 against the proximal bias of retracting spring 54 and safety shield 26 biased distally by spring 96 such that operating member 134 abuts plate 40 and is disposed distally of trigger 76. The plate 40 is disposed at the proximal ends of slots 130, and the retracting mechanism is prevented from moving proximally by latch 60. The trocar unit formed by the trocar, the safety shield and the hub is then combined with the portal unit passing the safety shield through the housing 29 via the opening in end wall 31 while simultaneously opening valve 41, and through the portal sleeve 24. With the front wall 44 of hub 28 abutting the end wall 31 of housing 29, the sharp tip of the trocar will protrude beyond the peripheral edge 106 of the portal sleeve and the peripheral edge 84 of the safety shield will protrude beyond and protect the sharp tip 32 of the trocar.

According to a method of operation for the retractable trocar with safety shield 120, latch 60 is normally in the position shown in FIG. 6 with trigger 76 in the rest position and finger 68 engaging a proximal face of plate 40 such that the retracting mechanism cannot move proximally and is, therefore, locked with the trocar 22 being prevented from moving proximally by the latch 60. Spring 96 is normally in the position shown in FIG. 6 such that the safety shield 26 is biased distally with the peripheral edge 84 of the safety shield protruding beyond the sharp tip 32 of the trocar prior to penetration of tissue of an anatomical cavity wall. When tissue of a cavity wall is to be penetrated, the hub 28 and housing 29 are gripped in one hand and the safety penetrating instrument is forced into the tissue. The safety shield 26 will move proximally against the distal bias of spring 96 due to the proximal force from tissue contact at the distal end of the retractable safety penetrating instrument such that the peripheral edge of the safety shield will be substantially aligned with the junction 36 of the trocar and the trailing edge 85 of the safety shield will be substantially aligned with the peripheral edge 106 of the portal sleeve. As the safety shield 26 moves proximally, the operating member 134 moves proximally past the trigger 76 urging the trigger clockwise looking at FIG. 6; however, this movement does not disengage the latch 60 from the plate 40 and the trigger returns to the rest position as soon as the operating member has moved proximally therepast. Once the distal end of the portal sleeve 24 has entered the anatomical cavity, such that the force from tissue contact is removed from the distal end of the retractable trocar with safety shield, the safety shield 26 will be moved distally due to the distal bias of spring 96. As the safety shield 26 moves distally, the operating member 134 moves distally such that edge 132 engages the trigger 76 and pulls the trigger distally causing the cam 72 to rotate counterclockwise looking at FIG. 6. With counterclockwise rotation of the cam 72, the actuating finger 138 pulls the contacting finger 136 in a direction outwardly from the longitudinal axis moving arm 66 outwardly in the direction of base 62 and releasing locking finger 68 from engagement with plate 40 of the retracting mechanism. Once released, the retracting mechanism will move proximally due to strong retracting spring 54 overriding the distal bias of the spring 96, and the retracting mechanism, via abutment of plate 40 with operating member 134, will carry the trocar 22 and the safety shield 26 proximally, the tube 46 guiding proximal movement of the trocar. With the trocar and the safety shield moved proximally by the retracting mechanism, the sharp tip 32 of the trocar is retracted within the distal end of the portal sleeve 24 and the operating member 134 is positioned proximally of trigger 76, the trigger having returned to the rest position. When it is desired to reset the retractable trocar with safety shield for further use, the trocar and retracting mechanism can be moved distally past the trigger 76 by moving knob 56 along slot 112 such that plate 40 is engaged and held by locking finger 68 of the latch 60. The trocar unit can be removed from the portal sleeve unit leaving the portal sleeve in place allowing insertion of additional instruments, irrigation, aspiration and other procedures to be conducted via the opening in the end wall 43 of valve housing 29.

It will be appreciated that rail 128 can have various cylindrical and non-cylindrical configurations, and that plate 40 can have various surface configurations, such as circular, rectangular and square, and can be provided with an extension or ledge extending perpendicularly in a proximal direction with the finger 68 engaging this ledge to prevent proximal movement of the retracting mechanism. The distance that the ledge extends proximally from the plate 40 can be varied to accommodate locking springs of various lengths and configurations and to control the distance that knob 56 must be slid along slot 112 before the finger 68 will engage the retracting mechanism when resetting the retractable trocar with safety shield. The rail can have the various configurations shown in applicant's co-pending patent application entitled "Retractable Safety Penetrating Instrument for Portal Sleeve Introduction" incorporated herein by reference.

Another modification of a retractable trocar with safety shield according to the present invention is illustrated in FIG. 7 at 140, a portion of the hub 28 of the retractable trocar with safety shield 140 being shown with the portion of the hub that is broken away being a mirror image of the portion shown. The retractable trocar with safety shield 140 includes hub 28 mounting trocar 22 and safety shield 26 concentrically disposed around the trocar 22. The safety shield 26 can be disposed concentrically within a portal sleeve 24 having a proximal end secured to a front wall 31 of the housing 29 as previously described. Trocar 22 includes a proximal end 42 disposed in hub 28 with cylindrical body 38 of the trocar passing through an aperture in a front wall 44 of the hub. A retracting mechanism is mounted on the proximal end 42 of the trocar 22 within hub 28 and includes a plate 40 extending outwardly from cylindrical body 38 perpendicular with a longitudinal axis of the retractable trocar with safety shield and an annular skirt 142 extending perpendicularly from plate 40 in a distal direction to define a rail 128 for mounting strong retracting spring 54. Plate 40 defines an abutment wall 50 parallel with front wall 44 of hub 28, and retracting spring 54 is disposed concentrically around trocar 22 within skirt 142 to be mounted in compression between front wall 44 of hub 28 and abutment wall 50 to bias the retracting mechanism in a proximal direction. The proximal end 42 of the trocar 22 is hollow to he mounted on a cylindrical member or tube 46 extending distally from end wall 48 of hub 28 and through an opening in plate 40 into the hollow proximal end 42 of the trocar. A locking and releasing mechanism 58 for the retracting mechanism is disposed in huh 28 and includes a latch having a locking bar 144 biased by a looking spring 60 into engagement with plate 40, a locking bar 144 and locking spring 60 being provided at diametrically opposite sides of tube 46. Locking bar 144 is pivotally secured at 146 to end wall 48 of huh 28 and extends angularly, distally toward a longitudinal axis of the retractable frocar with safety shield, the locking bar terminating distally at finger 68 angled in a direction outwardly from the longitudinal axis. Locking spring 60 biases the locking bar 144 in a direction inwardly toward the longitudinal axis such that the finger 68 engages plate 40 to prevent proximal movement of the trocar 22. Locking spring 60 includes a base 62 secured to a side wall of the huh 28 and extending distally to a bend 64 and an arm 66 extending angularly, proximally from bend 64 in the direction of the longitudinal axis. Arm 66 is bifurcated to define connecting webs 148 connecting spring 60 with fingers 68 to position the fingers in engagement with plate 40 and a releasing or trigger member including a trigger or leaf 76. Trigger 76 is spring-biased to a rest position shown in FIG. 7 wherein the trigger is disposed in the path of axial movement of an operating member on the safety shield 26 as will he explained further below. The safety shield 26 includes a proximal end disposed in huh 28 and terminating at an operating member or flange 134 positioned proximally of plate 40, the plate 40 extending through a longitudinal slot 130 formed in the cylindrical body of the safety shield 26, a pair of slots 130 being provided at diametrically opposite sides of the safety shield 26. Tube 46 passes through an opening in operating flange 134, and spring 96 is disposed concentrically around tube 46 and mounted in compression between operating flange 134 and end wall 48 of the hub 28 to bias the safety shield 26 in a distal direction.

According to a method of operation for retractable trocar with safety shield 140, the locking springs 60 are normally in the position shown in FIG. 7 with arms 66 biasing fingers 68 into engagement with plate 40 via webs 148 such that the trocar 22 cannot move proximally. Spring 96 is normally in the position shown in FIG. 7 such that the safety shield 26 is biased distally with operating flange 134 biased against plate 40. With the safety shield 26 biased distally, the peripheral edge of the safety shield 26 will protrude beyond the sharp tip of the trocar 22 at the distal end of the retractable safety penetrating instrument prior to penetration of tissue of an anatomical cavity wall. The trocar unit is combined with the portal sleeve unit, and the retractable safety penetrating instrument 140 is forced into tissue. The safety shield 26 will move proximally against the distal bias of spring 96 due to the proximal force from tissue contact at the distal end of the retractable trocar with safety shield such that the peripheral edge of the safety shield will be substantially aligned with the junction of the trocar and the trailing edge of the safety shield will be substantially aligned with the peripheral edge of the portal sleeve presenting a substantially smooth profile during penetration of tissue. Operating flange 134 will move proximally past the triggers 76 while the fingers 68 remain engaged with plate 40. Upon penetration of the distal end of the portal sleeve 24 into the anatomical cavity, the safety shield 26 will be moved distally due to the distal bias of spring 96; and, prior to the peripheral edge of the safety shield protruding beyond the sharp tip of the trocar, the operating flange 134 will engage the triggers 76 and pull the triggers distally forcing arms 66 of the locking springs 60 outwardly toward the bases 62 such that the fingers 68 are pulled by webs 148 in a direction outwardly from the longitudinal axis and out of engagement with plate 40. With fingers 68 disengaged from plate 40, the retracting mechanism and, therefore, the trocar 22, will be free to move proximally due to the proximal bias of strong retracting spring 54 overriding the distal bias of spring 96. The trocar 22 will carry the safety shield 26 proximal! y due to engagement of plate 40 with operating flange 134, the tube 46 guiding proximal movement of the trocar. With the trocar and safety shield proximally biased, the locking bars 144 will be disposed along skirt 142, and the sharp tip of the trocar 22 and the peripheral edge of the safety shield 26 will be disposed within the portal sleeve 24. The retractable trocar with safety shield 140 can be reset for further use by utilizing a knob and slot arrangement as previously described to move the trocar and the retracting mechanism distally until fingers 68 engage plate 40 and prevent retraction of the trocar.

A further modification of a retractable trocar with safety shield according to the present invention is illustrated in FIG. 8 at 150, a portion of the hub 28 of the retractable trocar with safety shield 150 being shown. The retractable trocar with safety shield 150 includes trocar 22, safety shield 26 concentrically disposed around trocar 22 and hub 28 mounting trocar 22 and safety shield 26. The safety shield can be disposed concentrically within a portal sleeve 24 having a proximal end secured to a front wall 31 of the housing 29 as previously described. The trocar 22 includes a proximal end 42 disposed in hub 28, and a retracting mechanism is mounted on the proximal end 42 of the trocar 22. The retracting mechanism includes a plate 40 extending outwardly from the cylindrical body 38 of the trocar perpendicular to a longitudinal axis of the retractable trocar with safety shield and a flat side 152 extending perpendicularly from plate 40 in a distal direction toward the front wall 44 of hub 28 to define a rail 128 for mounting retracting spring 54. Plate 40 defines an abutment wall 50 disposed parallel with front wall 44 of hub 28, and strong retracting spring 54 is disposed longitudinally in the rail 128 and mounted in compression between front wall 44 and abutment wall 50 to bias the retracting mechanism in a proximal direction. A locking and releasing mechanism 58 for the retracting mechanism is mounted in hub 28 and includes a latch or locking spring 60, as shown in FIG. 9, having a substantially flat base 64 secured to a side wall of hub 28, a distal bend 64 joined to base 62 and an arm 66 extending proximally from bend 64 parallel with a longitudinal axis of the retractable safety penetrating instrument. Arm 66 is bifurcated as shown in FIG. 9 to define a distally curved locking finger 68 extending in the direction of the longitudinal axis and a trigger or leaf 76 extending proximally of locking finger 68 and curved in the direction of the longitudinal axis. Locking finger 68 is spring biased into engagement with plate 40 such that the retracting mechanism and, therefore, the trocar 22, cannot move proximally. Trigger 76 is biased to a rest position shown in FIG. 8 wherein the trigger is disposed in the path of axial movement of the operating member on the safety shield 26 as will be explained further below. The safety shield 26 includes a proximal end 86 disposed in hub 28 and terminating at an operating member or flange 134, the plate 40 extending through a slot 130 in the cylindrical body of the safety shield such that the operating member 134 is disposed proximally of the plate 40, a pair of slots 130 being provided at diametric locations on the safety shield. Tube 46 extends distally from an end wall 48 of hub 28 and into the proximal end 42 of the trocar 22 via an opening in flange 134. Spring 96 is concentrically disposed around tube 46 and mounted in compression between flange 134 and end wall 48 to bias the safety shield 26 in a distal direction. With the safety shield 26 distally biased and the trocar 22 prevented from moving proximally, the peripheral edge of the safety shield 26 will protrude beyond the sharp tip of the trocar 22 at the distal end of the retractable safety penetrating instrument such that the sharp tip is protected prior to penetration of anatomical tissue. The trocar unit is combined with a portal sleeve unit and, when anatomical tissue is to be penetrated, the retractable safety penetrating instrument 150 is forced into the tissue causing the safety shield 26 to move proximally due to the proximal force from tissue contact at the distal end of the retractable safety penetrating instrument. With the safety shield 26 moved proximally, the peripheral edge of the safety shield 26 will be substantially aligned with the junction of the trocar 22 and the trailing edge of the safety shield will be substantially aligned with the peripheral edge of the portal sleeve 24 at the distal end of the retractable safety penetrating instrument. The operating member 134 will have moved proximally past the trigger 76; however, this movement does not disengage the locking finger 68 from plate 40 and the retracting mechanism remains locked. Upon penetration of the distal end of the portal sleeve 24 into the anatomical cavity, the safety shield 26 will move distally due to the distal bias of spring 96 such that the operating member 134 engages trigger 76 and pulls the trigger distally causing the arm 66 of locking spring 60 to be moved in a direction outwardly from the longitudinal axis and releasing finger 68 from engagement with plate 40. Once the retracting mechanism is released, the retracting spring 54 biases the trocar 22 proximally due to the strong retracting spring 54 overcoming the distal biased spring 96, and the trocar 22 carries the safety shield 26 proximally due to abutment of plate 40 with operating flange 134, with movement of the trocar being guided by tube 46. With the trocar 22 and safety shield 26 biased proximally, the sharp tip of the trocar 22 and the peripheral edge of the safety shield 26 will be disposed within the distal end of the portal sleeve 24. The retractable safety penetrating instrument 150 can be reset for further use by moving the trocar 22 distally via the knob and slot arrangement previously described such that plate 40 is engaged by finger 68 locking the trocar against proximal movement and allowing safety shield 26 to be biased distally by spring 96.

Another modification of a retractable safety penetrating instrument with safety shield according to the present invention is illustrated in FIG. 10 at 160. The retractable safety penetrating instrument 160 includes trocar .22, safety shield 26 concentrically disposed around trocar 22, portal sleeve 24 concentrically disposed around safety shield 26, hub 28 mounting trocar 22 and safety shield 26 and housing 29 mounting portal sleeve 24. The trocar 22 includes a distal end 30 having a conical configuration tapering distally to sharp tip 32 and proximally joined to cylindrical body 38 at junction 36 and a proximal end 42 disposed in hub 28. A thread. 161, shown in broken lines in FIG. 10, can be provided along conical distal end 30. The distal end 30 can be removably mounted on the cylindrical body 38 as shown in applicant's co-pending patent application previously referenced herein. Proximal end 42 terminates at a retracting mechanism including a plate 40 extending outwardly from cylindrical body 38 of the trocar 22 and a cylindrical rail 128 joined perpendicularly to plate 40 and extending proximally therefrom for mounting strong retracting spring 54. Rail 128 has an open distal end and a proximal end closed by abutment wall 50, .with the retracting spring 54 being disposed longitudinally within the rail 128 and mounted in compression between front wall 44 of hub 28 and abutment wall 50 to bias the retracting mechanism and, therefore, trocar 22, in a proximal direction. A locking and releasing mechanism 58 for the retracting mechanism is disposed in hub 28 and includes a latch or locking spring 60 having a substantially flat base 62 secured to a side wall of hub 28 and terminating proximally in a bend 64 adjacent end wall 48 and an arm 66 joined to bend 64 and extending angularly, distally from bend 64 in the direction of a longitudinal axis of the retractable safety penetrating instrument 160. A bent locking finger 68 on a distal end of the arm 66 engages plate 40 and holds the plate against front wall 44 of the hub 28 to prevent movement of the retracting mechanism and, therefore, the trocar 22, in a proximal direction. Arm 66 is bifurcated to form a releasing or trigger member including trigger or leaf 76 extending angularly, proximally in the direction of the longitudinal axis and spring biased to a rest position shown in FIG. 10. Safety shield 26 includes a distal end 80 beveled or angled from trailing edge 85 to peripheral edge 84 and proximal end 86 disposed in hub 28 and terminating at an operating member or flange 134 disposed proximally of plate 40, the plate 40 extending through longitudinal slots 130 in the cylindrical body 78 of the safety shield 26. Tube 46 extends distally from end wall 48 of hub 28 and through an opening in flange 134 into the hollow proximal end 42 of the trocar 22. Helical spring 96 is disposed around tube 46 and mounted in compression between operating flange 134 and end wall 48 to bias the safety shield 26 in a distal direction with flange 134 biased against plate 40. The portal sleeve 24 has a distal end 102 that can be angled or beveled at the same angle as the distal end 80 of safety shield 26, as shown at 104, terminating at a peripheral edge 106 and a proximal end 108 secured to a front wall of housing 29. A valve assembly 39 is mounted in housing 29 to control flow through the portal sleeve and the housing once the penetrating member unit is removed therefrom. The valve assembly 39 can have any acceptable configuration and, as shown, includes a flapper valve 41 biased to close off and seal an opening in an end wall 43 of the housing 29.

In order to assemble the retractable safety penetrating instrument 160, the proximal end 42 of the trocar 22 is assembled in hub 28 as shown in FIG. 10 with plate 40 of the retracting mechanism held against front wall 44 of hub 28 by latch 60 against the proximal bias of retracting spring 54. The safety shield 26 is disposed around the trocar 22, and spring 96 biases the safety shield 26 distally such that operating flange 134 is biased against plate 40 and the peripheral edge 84 of the safety shield protrudes beyond the sharp tip 32 of the trocar 22. The trocar unit formed by the trocar 22, the safety shield 26 and the hub 28 is then combined with the portal unit by passing the safety shield through the housing 29 via the opening in end wall 43, while simultaneously opening valve 41, and through the portal sleeve 24. With the front wall 44 of hub 28 abutting the end wall 43 of housing 29, the sharp tip 32 of the trocar protrudes beyond the peripheral edge of the portal sleeve 24 as shown in FIG. 10.

In a method of operation for the retractable safety penetrating instrument 160, the latch 60 is normally in the position shown in FIG. 10 with trigger 76 in a rest position spring-biased into the path of movement of the operating flange 134 and finger 68 engaging a proximal face of plate 40 such that the retracting mechanism cannot move proximally and is, therefore, locked with the plate 40 held against front wall 44 of hub 28. Spring 96 is normally in the position shown in FIG. 10 such that the safety shield 26 is biased distally with peripheral edge 84 of the safety shield protruding beyond the sharp tip 32 of the trocar prior to penetration of tissue of an anatomical cavity wall. When tissue of an anatomical cavity wall is to be penetrated, the hub 28 and housing 29 are gripped in one hand and the retractable safety penetrating instrument is forced into the tissue. The safety shield 26 will move proximally against the distal bias of spring 96 due to the proximal force from tissue contact at the distal end of the retractable safety penetrating instrument such that the peripheral edge 84 of the safety shield 26 will be substantially aligned with junction 36 of the trocar and the trailing edge 85 of the safety shield will be substantially aligned with the peripheral edge 106 of the portal sleeve 24 presenting a substantially smooth profile facilitating penetration of tissue and minimizing jamming and trapping of tissue. As the safety shield 26 moves proximally, operating flange 134 moves proximally past trigger 76; however, this movement does not disengage the latch 60 from the plate 40 and the trigger returns to the rest position as soon as the operating flange has moved proximally therepast. Once the distal end of the portal sleeve 24 has entered the anatomical cavity, such that the force from tissue contact is removed from the distal end of the retractable safety penetrating instrument, the safety shield 26 will be moved distally due to the distal bias of spring 96. As the safety shield 26 moves distally, operating flange 134 moves distally to engage the trigger 76 and pull the trigger distally causing the distal end of arm 66 to be bent or moved in a direction outwardly from the longitudinal axis such that finger 68 is released from plate 40.. Once released, the retracting mechanism will move proximally due to strong retracting spring 54 overriding the distal bias of spring 96, and the retracting mechanism will carry the trocar 22 and, via abutment of plate 40 with operating flange 134, the safety shield 26, proximally, the tube 46 guiding proximal movement of the trocar. With the trocar 22 and the safety shield 26 biased proximally by the retracting mechanism, the peripheral edge 84 of the safety shield 26 and the sharp tip 32 of the trocar 22 will be disposed within the distal end 102 of the portal sleeve 24. The operating flange 134 will be positioned proximally of trigger 76, the trigger having returned to the rest position. The retractable safety penetrating instrument can be reset for further use with a knob end slot mechanism as previously described.

Most complications from introduction of a portal sleeve into an anatomical cavity with a trocar result from the surgeon not using a smooth, continuous movement in forcing the trocar through the cavity wall. That is, when the penetrating movement is jerky or not smoothly continuous, entry into the cavity is frequently accomplished with too much force resulting in undesirable contact with tissue or organ structures in the cavity even if safety penetrating instruments are used; and, additionally, a jerky, discontinuous movement creates uneven tissue tearing rather than the minimal incision sought with endoscopic or least invasive surgery. One of the advantages of the present invention is that use of the retractable safety penetrating instrument with safety shield encourages a smooth, continuous penetrating movement by the surgeon in that should the surgeon use a jerky penetrating movement the trocar will retract within the portal sleeve due to the proximal movement of the retractable safety penetrating instrument by the surgeon. That is, when the surgeon moves the retractable safety penetrating instrument proximally or rearwardly, as occurs when the surgeon is hesitant or unsure, the safety shield and, therefore, the operating member, will move distally to trigger retraction of the trocar. Thus, the retractable safety penetrating instrument not only provides safe penetration of an anatomical cavity but also assures proper use of the penetrating instrument to minimize trauma. Another advantage of the present invention is that upon penetration of an anatomical cavity, the distal end of the safety shield will be retracted within the portal sleeve prior to the distal end of the safety shield protruding beyond the sharp tip of the trocar thusly protecting tissue and organ structures that could be damaged by even a blunt instrument part. The retractable safety penetrating instrument with safety shield of the present invention includes a portal sleeve receiving a trocar having a sharp distal tip protruding beyond a distal end of the portal sleeve for penetrating tissue and a safety shield disposed between the portal sleeve and the trocar and having a distal end biased to protrude beyond the sharp tip of the trocar, the trocar and safety shield being retractable to a protected position via a trigger responsive to movement of the safety shield distally upon entering a body cavity. The safety shield can be biased by springs or other suitable devices, including sponges and rubber, for applying a biasing force, and biasing devices can be axially aligned with or mounted laterally of the safety shield. The retracting spring for moving the trocar proximally can be mounted externally of, concentrically around or within the trocar, and various rail configurations can be employed to mount the retracting spring externally of the trocar. The locking mechanism for preventing movement of the trocar proximally can include a variety of latches or springs, and the release mechanism can include cams, spring-like members or any suitable means for releasing or locking mechanism by an action to move the latch or lock member out of the path of movement of the trocar or a rail movable therewith, such as in camming, spring, bending or buckling type actions and the like. The locking and releasing mechanism can be of multi-part or integral, unitary construction. The trocar must be securely held or locked in position prior to triggering of the retracting mechanism; and, thus, the latch members are preferably secured to the hub and can include multi-part or unitary flexible spring members operated by leaves or cams as well as pivoted rigid members secured to the housing. The operating member can include a variety of components, such as flanges, plates and arms, extending from the cylindrical body of the safety shield or the operating member can be formed as a wall of the cylindrical body. The sharp distal end of the trocar can have various solid or hollow geometrical configurations, and the distal end of the trocar can be interchangeably mounted on the cylindrical body of the trocar.

Having described preferred and alternative embodiments of a new and improved retractable safety penetrating instrument with safety shield, it is believed that other modifications, variations and changes will be suggested to those skilled in the art in view the teachings set forth herein. It is therefore to be understood that all such variations, modifications and changes are believed to fall within the scope of the present invention as defined by the appended claims.

What is claimed is:

1. A retractable safety penetrating instrument for forming a portal communicating with a cavity in the body to allow passage of instruments for performing least invasive medical procedures comprising a portal sleeve for providing a passage through a cavity wall and having a distal end for positioning in the body cavity, a proximal end for positioning externally of the body cavity and a lumen extending between said distal and proximal ends;

a penetrating member disposed in said lumen of said portal sleeve and having a sharp distal end for penetrating the cavity wall;

a safety shield disposed between said portal sleeve and said penetrating member and having a distal end protruding beyond the sharp distal end of the penetrating member;

retracting means for moving said penetrating member proximally relative to said portal sleeve from an extended position where said sharp distal end protrudes beyond said portal sleeve distal end to is a retracted position to prevent contact of said sharp distal end with tissue; and trigger means for automatically actuating said retracting means to move said penetrating member to a retracted position in response to movement of said safety shield distally upon said portal sleeve distal end entering the body cavity whereby said sharp distal end of said penetrating member is protected from inadvertent contact with tissue in the body cavity.

2. A retractable safety penetrating instrument as recited in claim 1 wherein said retracting means includes means for biasing said penetrating member in a proximal direction.

3. A retractable safety penetrating instrument as recited in claim 2 further including means engageable with said retracting means for preventing movement of said penetrating member in the proximal direction and said trigger means includes means for automatically disengaging said movement preventing means.

4. A retractable safety penetrating instrument for forming a portal communicating with a cavity in the body to allow passage of instruments for performing least invasive medical procedures comprising a portal sleeve for providing a passage through a cavity wall and having a distal end for positioning in the body cavity, a proximal end for positioning externally of the body cavity and a lumen extending between said distal and proximal ends;

a penetrating member disposed in said lumen of said portal sleeve and having a sharp distal end for penetrating the cavity wall and a hollow proximal end;

a safety shield disposed between said portal sleeve and said penetrating member and having a distal end protruding beyond the sharp distal end of the penetrating member;

retracting means for moving said penetrating member proximally relative to said portal sleeve from an extended position where said sharp distal end protrudes beyond said portal sleeve distal end to a retracted position to prevent contact of said sharp distal end with tissue, said retracting means including means for biasing said penetrating member in a proximal direction;

means engageable with said retracting means for preventing movement of said penetrating member in the proximal direction;

trigger means for automatically actuating said retracting means to move said penetrating member to a retracted position in response to movement of said safety shield distally upon said portal sleeve distal end entering the body cavity whereby said sharp distal end of said penetrating member is protected from inadvertent contact with tissue in the body cavity, said trigger means including means for automatically disengaging said movement preventing means; and hub means for mounting said proximal end of said penetrating member and cylindrical member means secured to said hub means and extending into said penetrating member proximal end for guiding proximal movement of said penetrating member.

5. A retractable safety penetrating instrument as recited in claim 4 wherein said biasing means includes a spring disposed within said penetrating member proximal end concentrically around said cylindrical member means.

6. A retractable safety penetrating instrument as recited in claim 5 further including a rim on said cylindrical member means disposed within said proximal end of said penetrating member and a shoulder on said proximal end of said penetrating member, said spring being mounted in compression between said rim and said shoulder.

7. A retractable safety penetrating instrument as recited in claim 4 wherein said biasing means is disposed within said hub means externally of said penetrating member proximal end.

8. A retractable safety penetrating instrument as recited in claim 7 further including rail means mounted externally on said proximal end of said penetrating member and having an abutment wall, and said biasing means includes a spring mounted in compression between said hub means and said abutment wall.

9. A retractable safety penetrating instrument as recited in claim 8 wherein said safety shield includes a cylindrical body terminating at a proximal end within said hub means and a longitudinal slot in said cylindrical body and further including a plate joined to said rail means and said penetrating member, said plate extending through said slot in said cylindrical body.

10. A retractable safety penetrating instrument as recited in claim 9 wherein said rail means includes a hollow cylinder having an end closed by said abutment wall and said spring is disposed concentrically within said cylinder.

11. A retractable safety penetrating instrument as recited in claim 9 wherein said rail means includes a flat side extending perpendicularly from said abutment wall and said spring is disposed laterally between said flat and said penetrating member.

12. A retractable safety penetrating instrument as recited in claim 4 wherein said biasing means includes a spring disposed concentrically around said penetrating member.

13. A retractable safety penetrating instrument as recited in claim 12 further including an abutment wall extending outwardly from said proximal end of said penetrating member and an annular skirt disposed concentrically around said proximal end of said penetrating member extending distally from said abutment wall, said spring being disposed concentrically around said penetrating member proximal end within said skirt and maintained in compression between said hub means and said abutment wall.

14. A retractable safety penetrating instrument as recited in claim 13 wherein said safety shield includes a cylindrical body terminating at a proximal end within said hub means and a longitudinal slot in said cylindrical body, said abutment wall extending through said slot.

15. A retractable safety penetrating instrument for forming a portal communicating with a cavity in the body to allow passage of instruments for performing least invasive medical procedures comprising a portal sleeve for providing a passage through a cavity wall and having a distal end for positioning in the body cavity, a proximal end for positioning externally of the body cavity and a lumen extending between said distal and proximal ends;

a penetrating member disposed in said lumen of said portal sleeve and having a sharp distal end for penetrating the cavity wall;

a safety shield disposed between said portal sleeve and said penetrating member and having a distal end protruding beyond said sharp distal end of said penetrating member;

retracting means for moving said safety shield and penetrating member proximally relative to said portal sleeve from an extended position where said distal ends of said safety shield and penetrating member protrude beyond said portal sleeve distal end to a retracted position within said portal sleeve; and trigger means including an operating member movable proximally as said penetrating member penetrates the cavity wall and movable distally thereafter, said trigger means being responsive to said distal movement of said operating member to actuate said retracting means to move said safety shield and penetrating member to said retracted position.

16. A retractable safety penetrating instrument as recited in claim 15 further including means for permitting said safety shield to move proximally as said penetrating member penetrates the cavity wall and wherein said operating member is disposed on said safety shield.

17. A retractable safety penetrating instrument as recited in claim 16 wherein said penetrating member includes a distal end surface joined to a cylindrical body at a junction, said distal end of said portal sleeve includes a peripheral edge and said distal end of said safety shield includes a trailing edge aligned with said portal sleeve peripheral edge and a peripheral edge aligned with said junction when said safety shield moves proximally as said penetrating member penetrates the cavity wall.

18. A retractable safety penetrating instrument as recited in claim 16 wherein said means for permitting said safety shield to move proximally includes means for biasing said safety shield in a distal direction.

19. A retractable safety penetrating instrument as recited in claim 18 wherein said penetrating member includes a hollow proximal end and further including hub means for mounting said proximal end of said trocar and cylindrical member means secured to said hub means and extending into said proximal end of said penetrating member, and wherein said safety shield includes a proximal end and said means for biasing includes a spring disposed concentrically around said cylindrical member means and mounted in compression between said safety shield proximal end and said hub means.

20. A retractable safety penetrating instrument as recited in claim 16 wherein said safety shield includes a proximal end and said operating member includes an arm on said proximal end of said safety shield.

21. A retractable safety penetrating instrument as recited in claim 16 wherein said safety shield includes a proximal end and said operating member includes a flange mounted on said proximal end of said safety shield.

22. A retractable safety penetrating instrument as recited in claim 16 wherein said safety shield includes a cylindrical body and said operating member includes a wall of said cylindrical body.

23. A retractable safety penetrating instrument as recited in claim 22 further including a longitudinal slot in said cylindrical body and wherein said operating member includes an edge on said wall defined by said longitudinal slot.

24. A retractable safety penetrating instrument as recited in claim 15 wherein said retracting means includes means for biasing said penetrating member proximally and further including locking means engagable with said retracting means for preventing movement of said retracting means proximally, said trigger means further including releasing means for being engaged by said operating member when said operating member moves distally for disengaging said locking means from said retracting means.

25. A retractable safety penetrating instrument as recited in claim 24 wherein said locking means includes a latch biased into engagement with said retracting means.

26. A retractable safety penetrating instrument as recited in claim 25 wherein said latch includes a spring.

27. A retractable safety penetrating instrument as recited in claim 26 wherein said releasing means includes cam means for disengaging said latch from said retracting means.

28. A retractable safety penetrating instrument as recited in claim 27 wherein said releasing means further includes a trigger on said cam means for being engaged by said operating member when said operating member moves distally.

29. A retractable safety penetrating instrument as recited in claim 28 wherein said cam means is biased to a rest position wherein said trigger is disposed within the path of distal movement of said operating member.

30. A retractable safety penetrating instrument as recited in claim 26 wherein said releasing means includes a trigger on said spring biased into the path of distal movement of said operating member.

31. A retractable safety penetrating instrument as recited in claim 25 wherein said latch includes a locking bar and said releasing means includes spring means for biasing said locking bar into engagement with said retracting means and disengaging said locking bar from said retracting means in response to distal movement of said operating member and a trigger on said spring means biased into the path of distal movement of said operating member.

32. A retractable safety penetrating instrument as recited in claim 24 wherein said locking means and said releasing means are of integral, unitary construction.

33. A retractable safety penetrating instrument as recited in claim 24 wherein said locking means and said releasing means are of multi-part construction.

34. A retractable safety penetrating instrument as recited in claim 33 further including hub means for mounting said penetrating member and said safety shield and housing means for mounting said portal sleeve, said hub means being removably engageable with said housing means allowing said penetrating member and safety shield to be removed form said portal sleeve allowing said portal sleeve to remain in the cavity.

35. A retractable safety penetrating instrument as recited in claim 34, further including valve means in said housing means for controlling flow through said portal sleeve.

36. A retractable safety penetrating instrument for forming a portal communicating with a cavity in the body to allow passage of instruments for performing least invasive medical procedures comprising
- a portal sleeve for providing a passage through a cavity wall and having a distal end for positioning in the body cavity, a proximal end for positioning exteriorly of the body cavity and a lumen extending between said distal and proximal ends;
- a penetrating member disposed in said lumen of said portal sleeve and having a sharp distal end for penetrating the cavity wall;
- a safety shield disposed in said lumen of said portal sleeve between said portal sleeve and said penetrating member and having a distal end;
- means for biasing said safety shield distally within said lumen of said portal sleeve to an extended position where said safety shield distal end protrudes beyond said sharp distal end of said penetrating member;
- retracting means for moving said penetrating member proximally relative to said portal sleeve to a retracted position within said retractable safety penetrating instrument in response to distal movement of said safety shield upon penetration into the body cavity; and
- trigger means for automatically actuating said retracting means to move said penetrating member to said retracted position in response to movement of said safety shield distally upon said portal sleeve distal end entering the body cavity whereby said penetrating member is moved to said retracted position prior to said safety shield distal end protruding beyond said sharp distal end of said penetrating member.

37. A retractable safety penetrating instrument as recited in claim 36 further including means for selectively moving said penetrating member form said retracted position to said extended position.

38. A retractable safety penetrating instrument as recited in claim 37 further including hub means for mounting said penetrating member and wherein said means for selectively moving includes knob means on said penetrating member and slot means in said hub means for receiving said knob means, said knob means being movable along said slot means to move said penetrating member from said retracted position to said extended position.

39. A retractable safety penetrating instrument as recited in claim 38 further including means for selectively locking said penetrating member in said extended position.

40. A retractable safety penetrating instrument for forming a portal communicating with a cavity in the body to allow passage of instruments for performing least invasive medical procedures comprising
- a portal sleeve for providing a passage through a cavity wall and having a distal end for positioning in the body cavity, a proximal end for positioning exteriorly of the body cavity and a lumen extending between said distal and proximal ends;
- a penetrating member disposed in said lumen of said portal sleeve and having a sharp distal end for penetrating the cavity wall;
- a safety shield disposed in said lumen of said portal sleeve between said portal sleeve and said penetrating member and having a distal end;
- means for biasing said safety shield distally within said lumen of said portal sleeve to an extended position where said safety shield distal end protrudes beyond said sharp distal end of said penetrating member;
- retracting means for moving said penetrating member proximally relative to said portal sleeve to a retracted position within said retractable safety penetrating instrument in response to distal movement of said safety shield upon penetration into the body cavity;
- trigger means for automatically actuating said retracting means to move said penetrating member to said retracted position in response to movement of said safety shield distally upon said portal sleeve distal end entering the body cavity whereby said penetrating member to moved to said retracted position prior to said safety shield protruding beyond said sharp distal end of said penetrating member;
- means for selectively moving said penetrating member form said retracted position to said extended position;
- hub means for mounting said penetrating member and wherein said means for selectively moving includes knob means on said penetrating member and slot means in said hub means for receiving said knob means, said knob means being movable along said slot means to move said penetrating member form said retracted position to said extended position; and
- means for selectively locking said penetrating member in said extended position, said means for locking including a locking member pivotally mounted on said hub means for being selectively moved into a position preventing proximal movement of said knob means along said slot means.

* * * * *